United States Patent
Ramachandran

(10) Patent No.: US 8,457,906 B2
(45) Date of Patent: Jun. 4, 2013

(54) CORROSION AND EROSION CORROSION TYPE DETERMINATION FROM PARAMETRIC SHAPE REPRESENTATION OF SURFACES

(75) Inventor: Sunder Ramachandran, Sugar Land, TX (US)

(73) Assignee: Baker Hughes Incorporated, Houston, TX (US)

( * ) Notice: Subject to any disclaimer, the term of this patent is extended or adjusted under 35 U.S.C. 154(b) by 767 days.

(21) Appl. No.: 12/526,024

(22) PCT Filed: Jan. 28, 2008

(86) PCT No.: PCT/US2008/052153
§ 371 (c)(1),
(2), (4) Date: Aug. 5, 2009

(87) PCT Pub. No.: WO2008/134100
PCT Pub. Date: Nov. 6, 2008

(65) Prior Publication Data
US 2010/0324836 A1      Dec. 23, 2010

Related U.S. Application Data

(60) Provisional application No. 60/888,123, filed on Feb. 5, 2007.

(51) Int. Cl.
*G01N 17/00*      (2006.01)

(52) U.S. Cl.
USPC .............................................. 702/35; 702/34

(58) Field of Classification Search
USPC ........................................................ 702/34, 35
See application file for complete search history.

(56) References Cited

U.S. PATENT DOCUMENTS

| | | | | |
|---|---|---|---|---|
| 5,614,720 A | * | 3/1997 | Morgan et al. | 250/360.1 |
| 2005/0182613 A1 | * | 8/2005 | Kwun et al. | 703/18 |
| 2006/0288756 A1 | * | 12/2006 | De Meurechy | 73/1.01 |
| 2007/0059436 A1 | * | 3/2007 | Dikun | 427/2.26 |
| 2007/0140547 A1 | * | 6/2007 | Eswara et al. | 382/141 |
| 2008/0183402 A1 | * | 7/2008 | Malkin et al. | 702/34 |

* cited by examiner

*Primary Examiner* — Andrew Schechter
*Assistant Examiner* — Haidong Zhang
(74) *Attorney, Agent, or Firm* — Mossman Kumar & Tyler PC

(57) ABSTRACT

Different types of localized corrosion, erosion corrosion and other types of corrosion may be detected and identified by examining or viewing a solid surface where corrosion is occurring or has occurred to obtain an image therefrom. The image is then represented as a three-dimensional mathematical surface, which is then fit to a parametric surface composed of one or more curved and/or polygonal surfaces. Representative parameters are determined from the parametric surface. The corrosion type is identified by the best fit of the parameters known to be correlated (or caused by) a particular type of corrosive activity or agent for a given substrate.

4 Claims, 3 Drawing Sheets

US 8,457,906 B2

CORROSION AND EROSION CORROSION TYPE DETERMINATION FROM PARAMETRIC SHAPE REPRESENTATION OF SURFACES

TECHNICAL FIELD

The present invention relates to methods and systems for determining corrosion types, and more particularly relates in one non-limiting embodiment to methods, techniques and systems for identifying, evaluating and distinguishing between different corrosion types, such as, but not limited to, localized corrosion and erosion corrosion.

TECHNICAL BACKGROUND

Localized corrosion of equipment is a serious problem in many industries and processes. In particular, corrosion failures in many oil and gas production systems, oil/gas/water transmission pipelines, petrochemical and chemical processing plants, fossil fuel and nuclear power plants are in the form of localized corrosion. Localized corrosion may result in loss of production, increase in maintenance cost, environmental pollution and potential health and safety hazards, etc. It is important that the occurrence of localized corrosion is identified and the severity determined in advance of structural failure, particularly catastrophic failure. In addition, the ability of chemicals to inhibit localized corrosion needs to be determined.

Localized corrosion is the selective removal of metal by corrosion at small areas or zones on a metal surface in contact with a corrosive environment, usually a liquid. While pitting is a type of localized corrosion, the locally corrosive pits may eventually cover substantial portions of a corroded electrically conductive article's surface. Localized corrosion may occur when small local sites are attacked at a much higher rate than the rest of the surface. Localized corrosion occurs when corrosion works with other destructive forces such as stress, fatigue, erosion and chemical attacks. Localized corrosion can cause more damage than any of these destructive forces individually.

The problems resulting from localized corrosion have been dealt with for many years with variable success. Localized corrosion is highly stochastic in nature and its occurrence is fairly unpredictable. Currently, localized corrosion is studied or monitored by measuring directly relatively large features (e.g. pits) on the surface by using standard optical microscopy with limited spatial resolution. Indirect methods are also used, such as electrochemical noise, to characterize localized (e.g. localization index) corrosion.

Erosion corrosion is the corrosion of a metal which is caused or accelerated by the relative motion of the environment and the metal surface, particularly when small particles, e.g. sand, contacts the metal surface. Erosion corrosion may also be caused by fluids, such as gases (e.g. air, natural gas, etc.) and liquids (e.g. water, oil, etc.) Erosion corrosion is characterized by surface features with a directional pattern which are a direct result of the flowing media. Erosion corrosion is most prevalent in soft alloys (e.g. copper, aluminum and lead alloys), although others may be affected. Alloys which form a surface film in a corrosive environment commonly show a limiting velocity above which corrosion rapidly accelerates. Other factors such as turbulence, cavitation, impingement or galvanic effects can add to the severity of attack. Erosion corrosion is a type of corrosion produced when easily removed scales (e.g. iron carbonate) that were initially protecting the metals in the pipe are eroded and the underlying metals are corroded. Erosion corrosion is a common cause of failure in oilfield equipment. The erosive attack is often localized at changes of pipe sections, bends or elbows where there is high velocity and/or turbulent flow.

Electrochemical noise (ECN) may be defined as the spontaneous fluctuations of current and potential generated by corrosion reactions. Various methods have been used to determine corrosion rates, including a linear polarization resistance (LPR) method. In LPR a direct current (DC) signal is applied to a corroding cell consisting of two or three electrodes and the resulting DC polarization is monitored. Provided that the applied current is small and that the potential shift is less than 20 millivolts (mV), the response is linear in most cases and the measured resistance, commonly known as the polarization resistance, may be related inversely to the rate of the uniform corrosion attack. Other techniques include the application of electrochemical impedance spectroscopy (EIS) in which a sine wave current or potential is applied, in a manner similar to the linear polarization technique, and the sine wave potential or current resulting from the applied current or potential is monitored. Alternatively, a pseudo random noise signal can be applied to a corroding cell, with the electrochemical impedance obtained by time or frequency domain transformations.

Although the above techniques are widely employed, they: (1) possess limitations in that they only provide information on uniform (general) corrosion conditions because they provide an average signal for the surface of the electrode being monitored; and (2) depending upon the environment, metallic material, and corrosion type, the assumption that the corrosion rate is inversely proportional to the measured charge transfer or polarization resistance may be invalid because the corrosion is of a localized nature.

Of general background interest are U.S. Patent Application Publication 2004/0031337 A1 which relates broadly to systems of addressing pipeline anomalies prior to failure of pipeline integrity. In particular, a pipeline inspection system integrates a serviceability acceptance criteria for pipeline anomalies, specifically wrinkles, with a method of correlating ultrasonic test data to actual anomaly characteristics. U.S. Patent Application Publication 2004/0100256 A1 concerns an inspection system for detecting flaws in oil and gas well borehole ferromagnetic tubular goods. The inspection device operates inside the tubular by first saturating a tubular wall with magnetic flux. Flaws in the wall causes flux leakage, and the magnitudes of the flux leakages are measured with Hall effect sensors disposed within the inspection device. The magnitude of flux leakage is then related to the amount of ferromagnetic material loss resulting from the flaw. Eddy currents induced in the wall are also measured and combined with the Hall effect sensor measurements to define location and geometric shape of the flaw.

It would be advantageous if new methods and systems were devised to determine and/or identify corrosion types so that efforts or techniques could be taken or employed to inhibit or prevent the identified corrosion type from continuing or occurring in the first place.

SUMMARY

Image analysis through a means such as optical microscopy can obtain an image from which a surface of the image is obtained. There is provided, in one form, a method for identifying corrosion types, where the method involves examining a solid surface having corrosion to obtain at least one image. The method then includes representing the image as a three-dimensional mathematical surface, and fitting the three-dimensional mathematical surface to a parametric surface composed of one or more different curved and/or polygonal shapes. Finally, the method involves determining representative parameters from the parametric surface and identifying a corrosion type by the best fit of the representative parameters known to be correlated to a particular corrosion type.

There is additionally provided in a non-restrictive version, a system for identifying corrosion types, where the system involves an examination subsystem that examines a solid surface having corrosion to obtain at least one image. The system further includes a modeling subsystem that represents the image as a three-dimensional mathematical surface. The system also concerns an analysis subsystem that is configured to fit the three-dimensional mathematical surface to a parametric surface composed of one or more curved and/or polygonal shapes, determine representative parameters from the parametric surface and also identify a corrosion type by the best fit of the representative parameters known to be correlated to a particular corrosion type.

Figure 1:
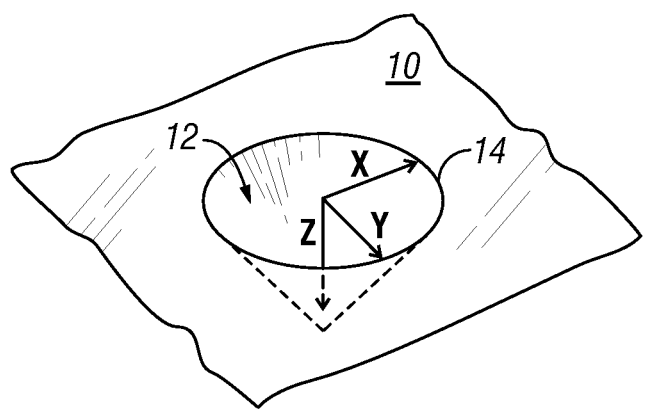
FIG. 1 is a schematic three-dimensional, perspective representation of a parametric surface of a single cone-shaped corrosion pit or indentation.

It will be appreciated that the Figures are not necessarily to any scale, and represent relatively small features on a substrate that would be difficult to see or determine anything about without a microscope or other type of microscopic examination.

DETAILED DESCRIPTION

A surface image of a solid surface may be obtained by different methods. One method is optical microscopy. The image obtained may be represented as a three-dimensional mathematical surface. This image may then be fitted or matched to any parametric surface, such as one composed of more than one curved or polygonal surface.

One of the most general parametric surfaces is a number of cut ellipsoids. In general, the best-fit surface would determine the parameters. The parameters of the surface are related to its cause. Non-limiting examples include the hydrogen sulfide ($H_2S$) and/or carbon dioxide ($CO_2$) corrosion of mild steel. Other types of iron alloys and different metal alloys may be studied in a similar manner. The amorphous or crystalline structure of the substrate being corroded may also affect the shape of the parametric surface and its corresponding three-dimensional mathematical surface. When the pattern of the surface is identified and found to be in a parameter set accompanied by a type of corrosion (e.g. $CO_2$ corrosion), the cause may be determined. The correlation of the parametric surface to a particular corrosion type or cause would be determined by a previous study of surface images and parametric surfaces of corrosion with known causes. This correlation simply involves matching the parametric surfaces to a particular corrosion type or cause in a sufficiently thorough study of known corrosion processes. The invention herein thus relates to a technique that determines mathematical parameters of the surface and then determines the type of corrosion based upon these values. The methods and systems herein are analogous to developing a "fingerprint" database of parametric surfaces caused by known corrosive forces, effects or agents for a particular substrate, and then the database is used to compare parametric surfaces from unknown causes to determine their cause or source of corrosion or corrosive activity.

The image is obtained by methods including, but not necessarily limited to, optical microscopy, interferometry, Hall effect sensors, magnetic flux sensors, ultrasonic measurements and combinations thereof. More specifically, image surfaces may be obtained from devices such as a Nikon Eclipse 60 microscope or a white light interferometer. Other suitable image collection devices include, but are not necessarily limited to intelligent pigs utilizing Hall effect sensors. As noted, magnetic flux or ultrasonic measurements and appropriate equipment to obtain them may also be employed.

For optical devices such as microscopes, software such as the Auto-Montage program (available from Syncroscopy division of Synoptics Group), in one non-limiting embodiment may be used to generate three-dimensional grids of the surface. An image surface may be represented as a three-dimensional locus of x, y and z coordinates. A set of points i may be represented with coordinates $x_i$, $y_i$ and $z_i$ in Cartesian coordinates on a surface, such as a surface that has been corroded. The z direction represents the depth into the surface, and thus the $z_i$ coordinate represents the depth of the image surface at position $(x_i, y_i)$. The methods herein assume that corrosion is manifested or exhibited as the removal or absence of material that was originally present at the surface.

Several parametric surfaces may be used to represent the actual surface. Among these are the following:
   a. parametric surface of n cones;
   b. parametric surface of n cut spheroids;
   c. parametric surface of n ellipsoids;
   d. parametric surface of n cylinders;
   e. parametric surfaces of n pyramids;
   f. and combinations thereof, where n represents the number of the given shapes.

The various mathematical representations of these surfaces are provided below. It will be appreciated that the functions could be different from those shown below as non-limiting embodiments. An oblique ellipsoid surface, an oblique cone surface, and an oblique cylinder surface have been conceptualized, but have not yet been mathematically represented. However, it will be appreciated that these may be mathematically represented similarly to the surfaces represented herein, although their representations would be expected to be more complex. The method would then calculate the sum of squares of the actual surface subtracted by the idealized function and determine parameters that minimize this function. This function can be multiplied by a variety of weighting functions if needed. Also functions that represent slope and waviness may be added to the functions described below, if waviness or slope is seen in the actual surface. Such functions may be subtracted so that they do not affect the focus on the functions describing the corrosion.

a) Parametric Surface of n Cones
z=0, if for all i cones from 1 to n $(x-x_i)^2+(y-y_i)^2>R_i^2$
When $(x-x_i)^2+(y-y_i)^2<R_i^2$ then:

$$z = \frac{h_i}{R_i}\left(R_i - \sqrt{(x-x_i)^2 + (y-y_i)^2}\right)$$

Where $R_i$, $h_i$, $x_i$ and $y_i$ are defined below.
b) Parametric Surface of n Cut Spheroids
z=0, if for all (i=1 to N) cut spheroids from 1 to n $(x-x_i)^2+(y-y_i)^2>R_i^2$
When $(x-x_i)^2+(y-y_i)^2<R_i^2$ then:

$$R_i' = \frac{h_i^2 + R_i^2}{2h_i}, \theta = \cos^{-1}\frac{\sqrt{(x-x_i)^2 + (y-y_i)^2}}{R_i'}, \theta_i = \cos^{-1}\frac{R_i}{R_i'}$$

$z=R_i'(\sin\theta - \sin\theta_i)$

Where $R_i$, $h_i$, $R'_i$, $\Theta_1$, $x_i$ and $y_i$ are defined below.
c) Parametric Surface of n Ellipsoids
z=0, if for all (i=1 to N) cut ellipsoids from 1 to n $$\frac{((x-x_i)\cos\theta_i - (y-y_i)\sin\theta_i)^2}{a_i^2} + \frac{((x-x_i)\sin\theta_i + (y-y_i)\cos\theta_i)^2}{b_i^2} > R_i^2$$

When $\frac{((x-x_i)\cos\theta_i(y-y_i)\sin\theta_i)^2}{a_i^2} + \frac{((x-x_i)\sin\theta_i + (y-y_i)\cos\theta_i)^2}{b_i^2} < R_i^2$ then $$z = c_i\left(\sqrt{\left(1 - \frac{((x-x_i)\cos\theta_i - (y-y_i)\sin\theta_i)^2}{a_i^2} - \frac{((x-x_i)\sin\theta_i - (y-y_i)\cos\theta_i)^2}{b_i}\right)}\right)$$

Where $R_i$, $h_i$, $\Theta_i$, $a_i$, $b_i$, $c_i$, $x_i$, and $y_i$ are defined below.
d) Parametric Surface of n Cylinders
z=0, if for all i cylinders from 1 to n $(x-x_i)^2+(y-y_i)^2>R_i^2$
When $(x-x_i)^2+(y-y_i)^2<R_i^2$ then:

$z=h_i$ where $R_i$, $h_i$, $x_i$ and $y_i$ are defined below.
e) Parametric Surface of n Pyramids
z=0 When for all i=n, $|x-x_i|>a_i$ or $|y-y_i|<b_i$
If for any j $|x-x_j|<a_j$ and $|y-y_j|<b_j$
Then If $|x-x_j|>|y-y_j|$ $$z = h_j - \frac{h_j|x-x_j|}{a_j} \text{ Or if } |y-y_j| > |x-x_j|$$

$$z = h_j - \frac{h_j|y-y_j|}{b_j}$$

where $h_j$, $a_j$, $b_j$, $x_i$ and $y_i$ are defined below.

The parameters of these surfaces may be obtained by minimizing the error function or any similar such function with respect to the parameters of the idealized surface. With a best fit the following parameters may be obtained for the different model functions noted above:
a) Parametric Surface of n Cones
Parameters:
n=number of cones,
$h_a$=depth of cone a,
$R_a$=radius of cone a,
$x_a$=x position of center of circle defining cone a, and
$y_a$=y position of center of circle defining cone a.
b) Parametric Surface of n Cut Spheroids
Parameters:
n=number of cut spheroids
$h_a$=depth of spheroid a,
$R_a$=radius of cut spheroid a,
$R'_a$=is the radius at which the spheroid is cut in the surface,
$\Theta_1$=is the angle at which this cut is made,
$x_a$=x position of center of circle defining spheroid a, and
$y_a$=y position of center of circle defining spheroid a.
c) Parametric Surface of n Cut Ellipsoids
Parameters:
n=number of cut ellipsoids,
$\Theta_i$=angle of inclination of axis set of ellipsoid i,
$a_i$=minor ellipse axis in x' direction of ellipsoid i,
$b_i$=major ellipse axis in y direction of ellipsoid i,
$c_i$=major ellipse axis in z direction of ellipsoid i, $$R_i = 1 - \frac{z_i^2}{c_i^2}$$

$x_i$=x position of center of circle defining ellipsoid I,
$y_i$=y position of center of circle defining ellipsoid I, and
$z_i$=z position of center of circle defining ellipsoid i.
d) Parametric Surface of n Cylinders
Parameters:
n=number of cylinders,
$h_a$=depth of $a^{th}$ cylinder, and
$R_a$=radius of $a^{th}$ cylinder
e) Parametric Surface of n pyramids
Parameters:
n=number of pyramids,
$h_a$=depth of $a^{th}$ pyramid,
$a_i$=half of the width of pyramid in x direction, and
$b_i$=half of the width of pyramid in y direction.
The parameters that will then distinguish corrosion for the different surfaces may be the following:
a) n Cones: $h_a/R_a$
b) n Cut Spheroids: $h_a/R_a$
c) n Cut Ellipsoids: $a_n/b_n$, $h_n/R_n$
d) n Cylinders: $h_n/R_n$
e) n Pyramids $a_j/b_j$, $h_j/a_j$, $h_j/b_j$
For each type of corrosion distinctive values are expected and these patterns or "fingerprints" may then be used to determine the type of corrosion being examined.

The best fit of the model function with the measured depth profile may be calculated using the function:

$$f = \sum_n (z_{measure} - z_{model})^2$$

Another function that can specify the fit of the model function with the measured function is shown below:

$$f_1 = \sum_n \frac{(z_{measure} - z_{model})^2}{z_{measure}}$$

For a choice of all parameters, functions f or $f_1$ can be computed. Either function f can then be optimized as a function of the different parameters using different algorithms such as those provided in Chapter 10 of "Numerical Recipes in Fortran: The Art of Scientific Computing" Second Edition by W. H. Press, S. A. Teukolosky, W. T. Vettering and B. P. Flannery, Cambridge University Press, copyright 1992, incorporated herein by reference. The process of optimization would vary the parameters characterizing each of our model functions to minimize either function f or $f_1$.

For each type of corrosion distinctive values are expected and these patterns or "fingerprints" may then be used to determine the type of corrosion being examined. Non-limiting examples of the different types of corrosion that may be characterized or identified by the various parameters noted above include, but are not necessarily limited to, the $CO_2$ corrosion of mild steel, $H_2S$ corrosion of mild steel, oxygen corrosion of mild steel, acid-producing bacterial corrosion of mild steel and/or mesa corrosion. Different types of corrosion may be characterized or identified for other substrates that may be corroded including, but not necessary limited to, other iron alloys and other metal alloys.

The various Figures will schematically illustrate how some of the various parametric surfaces might appear visually in simple representations. Actual corrosion may be composed of one or more of the surfaces shown, singly or in groups. Shown in FIG. 1 is a portion or section of planar surface 10, such as a mild steel surface, viewed from above at an angle, where a single conical pit 12 of localized corrosion is evident penetrating surface 10 in the z direction (a right cone), where the x and y directions or axes are also shown. Edge of conical pit 12 is shown at 14, seen as an ellipse in FIG. 1, although it might appear as a circle if viewed directly from above or in a direction normal to planar surface 10. An oblique cone is not shown in the Figures, but may be readily imagined.

Figure 2:
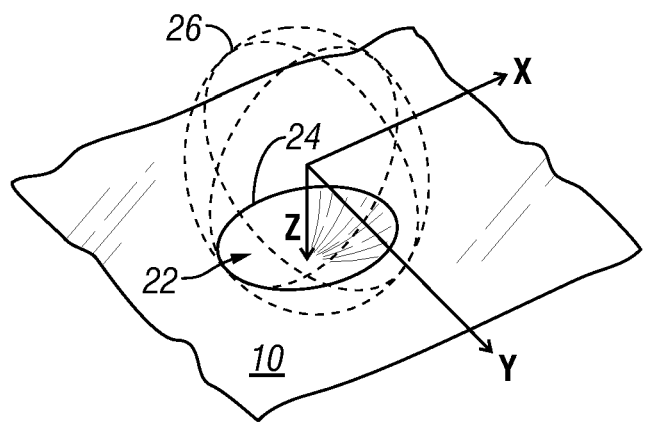
FIG. 2 is a schematic three-dimensional, perspective representation of a parametric surface of a single spheroid-shaped corrosion pit or indentation.

Shown in FIG. 2 is a portion or section of planar surface 10 bearing a single depression, crater, pit, or indentation 22 of localized corrosion evident penetrating or gouging surface 10 in the z direction, where the x and y directions or axes of a cut spheroid 26 are also shown. Edge of elliptical or circular pit 22 is shown at 24, seen as an ellipse in FIG. 2, although it might appear as a circle if viewed directly from above or in a direction normal to planar surface 10.

Figure 3:
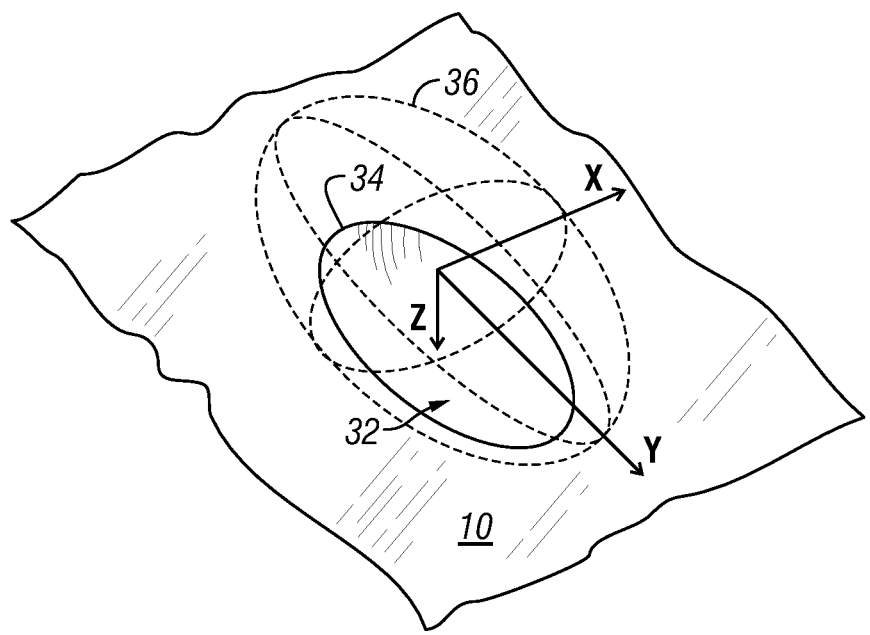
FIG. 3 is a schematic three-dimensional, perspective representation of a parametric surface of a single ellipsoid-shaped corrosion pit or indentation.

Shown in FIG. 3 is a portion or section of planar surface 10 bearing a single depression, crater, pit, or indentation 32 of localized corrosion evident penetrating or removed from surface 10 in the z direction, where the x and y directions or axes of a cut ellipsoid 36 are also shown. Edge of elliptical or circular pit 32 is shown at 34, seen as an ellipse in FIG. 3. Such edge would also appear as an ellipse if viewed directly from above or in a direction normal to planar surface 10.

Figure 4:
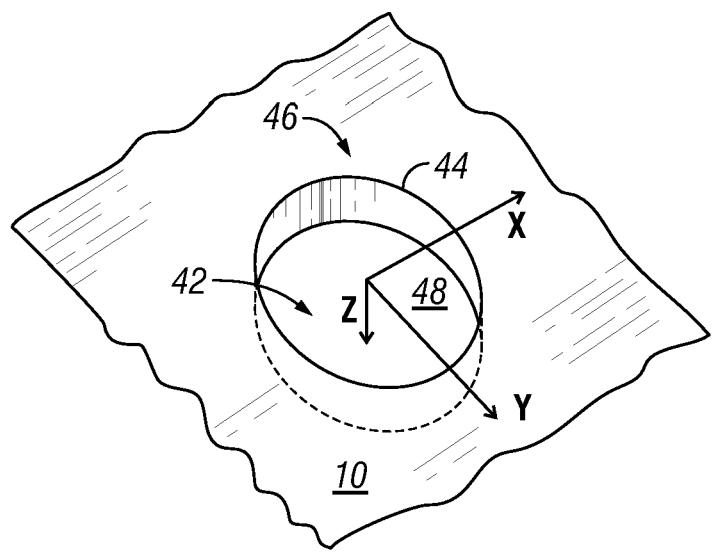
FIG. 4 is a schematic three-dimensional, perspective representation of a parametric surface of a single cylindrically shaped corrosion pit or indentation.

Shown in FIG. 4 is a portion or section of planar surface 10 bearing a single depression, crater, pit, or indentation 42 of localized corrosion evident penetrating or gouging surface 10 in the z direction, where the x and y directions or axes of a right cut cylinder 46 are also shown. Edge of elliptical or circular pit 42 is shown at 44, seen as an ellipse in FIG. 4. The floor of indentation 42 is shown at 48. Such edge might appear as a circle or an ellipse if viewed directly from above or in a direction normal to planar surface 10.

Figure 5:
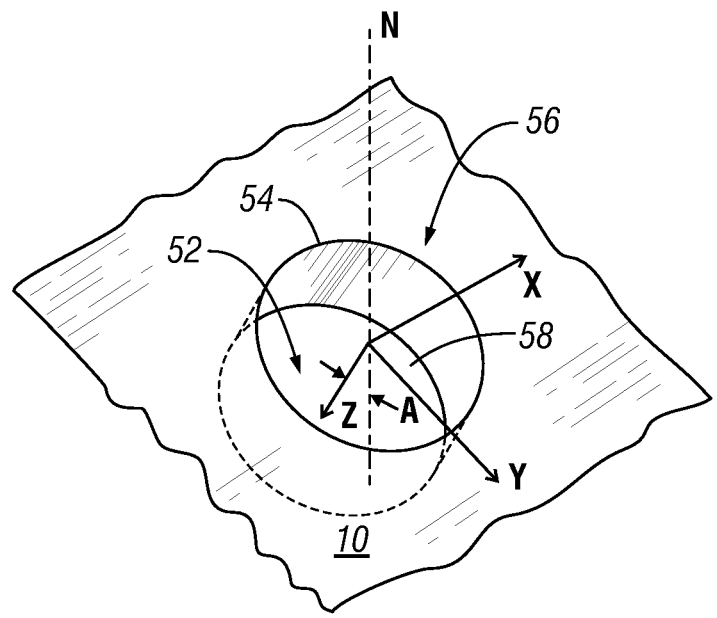
FIG. 5 is a schematic three-dimensional, perspective representation of a parametric surface of a single oblique cylinder-shaped corrosion pit or indentation.

Shown in FIG. 5 is a portion or section of planar surface 10 bearing a single depression, crater, pit, or indentation 52 of localized corrosion evident penetrating or removed from surface 10 in the z direction, where the x and y directions or axes of an oblique cut cylinder 56 are also shown. Edge of elliptical or circular pit 52 is shown at 54, seen as an ellipse in FIG. 5. The floor of indentation 52 is shown at 58. Such edge might appear as an ellipse if viewed directly from above or in a direction normal to planar surface 10. The z axis of cylinder 56 is at an angle A to the normal direction N of planar surface 10, thereby making the cylinder 56 oblique, as contrasted with cylinder 46 of FIG. 4.

Figure 6:
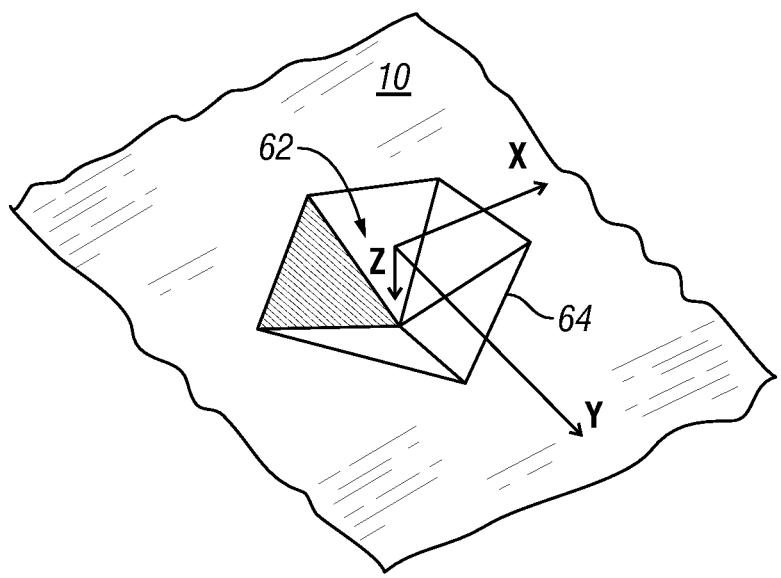
FIG. 6 is a schematic three-dimensional, perspective representation of a parametric surface of a single polyhedral or pyramidal-shaped corrosion pit or indentation.

Shown in FIG. 6 is a portion or section of planar surface 10, such as a mild steel surface, viewed from above at an angle, where a single polyhedral or pyramidal pit, crater, depression or indentation 62 of localized corrosion is evident penetrating surface 10 in the z direction (a right pyramid), where the x and y directions or axes are also shown. The edge of pyramidal pit is shown at 64, seen as an irregular polygon in FIG. 6. Edge 64 may also be seen as an irregular polygon if viewed directly from above or in a direction normal to planar surface 10. Of course, edge 64 may certain be a regular polygon when viewed from above in other embodiments not shown. The empty shape of pit 62 may be a regular or irregular pyramid, and although a right pyramid is shown in FIG. 6, an oblique pyramid may be easily imagined.

In practice, in a non-limiting, illustrative embodiment, if a particular type of localized corrosion is identified as being caused by the presence of $H_2S$, then steps may be taken to either reduce or eliminate the presence of $H_2S$, and/or introduce a $H_2S$ scavenger, and/or introduce a corrosion inhibitor known to be effective against $H_2S$ corrosion. The size, amount or frequency of these preventative or inhibitive methods may be designed or customized depending upon the severity of the corrosive attack as determined by the methods and systems described herein. Of course, it is expected that more than one corrosive force or agent may be operating on the surface being studied or examined, and thus, it may be necessary to implement methods or techniques to address more than one type of corrosive event or attack simultaneously.

Many modifications may be made in the methods and systems of this invention without departing from the scope thereof that are defined only in the appended claims. For example, the particular system design or method sequence may be different from those explicitly used and/or described here. Additionally, metals, corrosion inhibitors, corrosion types, imaging methods, parametric surfaces, etc. other than those specifically mentioned may find utility in the methods and systems of this invention. Various combinations of measuring or imaging systems or devices, metals, parametric surfaces, corrosion types, and corrosion inhibitors, besides those explicitly mentioned herein, and in different proportions than those mentioned herein, are also expected to find utility. Further, it is also expected that much of the method described herein may be implemented in software, including, but not necessarily limited to, representing the image as a three-dimensional mathematical surface, fitting the three-dimensional mathematical surface to a parametric surface composed of one or more curved and/or polygonal shapes, determining representative parameters from the parametric surface, and identifying a corrosion type by the best fit of the representative parameters known to be correlated to a particular corrosion type.

As used throughout the claims herein the words "comprising" and "comprises" is to be interpreted to mean "including but not limited to".

What is claimed is:

1. A method for identifying corrosion types, the method comprising:
   examining a solid surface having corrosion using an examination subsystem to obtain at least one image;
   representing the image as a three-dimensional mathematical surface using a modeling subsystem;
   using an analysis subsystem for:
      fitting the three-dimensional mathematical surface to a parametric surface composed of one or more curved and/or polygonal shapes, where the parametric surface is selected from the group consisting of:
      a. parametric surface of n cones;
      b. parametric surface of n cut spheroids;
      c. parametric surface of n ellipsoids;
      d. parametric surface of n cylinders;
      e. parametric surfaces of n pyramids; and
      f. combinations thereof,
      where n represents the number of indicated shapes in the parametric surface;
      determining representative parameters from the parametric surface; and
      identifying a corrosion type by the best fit of the representative parameters known to be correlated to a particular corrosion type, where the corrosion type is selected from the group consisting of:
      i. $CO_2$ corrosion of mild steel;
      ii. $H_2S$ corrosion of mild steel;
      iii. oxygen corrosion of mild steel;
      iv. acid-producing bacterial corrosion of mild steel;
      v. mesa corrosion; and
      vi. combinations thereof.

2. A method for identifying corrosion types, the method comprising:
   examining a solid surface having corrosion using an examination subsystem to obtain at least one image by a method selected from the group consisting of optical microscopy, interferometry, Hall effect sensors, magnetic flux sensors, ultrasonic measurements and combinations thereof;
   representing the image as a three-dimensional mathematical surface using a modeling subsystem;
   using an analysis subsystem for:
      fitting the three-dimensional mathematical surface to a parametric surface composed of one or more curved and/or polygonal shapes, where the parametric surface is selected from the group consisting of:
      a. parametric surface of n cones;
      b. parametric surface of n cut spheroids;
      c. parametric surface of n ellipsoids;
      d. parametric surface of n cylinders;
      e. parametric surfaces of n pyramids; and
      f. combinations thereof,
      where n represents the number of indicated shapes in the parametric surface
      determining representative parameters from the parametric surface; and
      identifying a corrosion type by the best fit of the representative parameters known to be correlated to a particular corrosion type, where the corrosion type is selected from the group consisting of:
      i. $CO_2$ corrosion of mild steel;
      ii. $H_2S$ corrosion of mild steel;
      iii. oxygen corrosion of mild steel;
      iv. acid-producing bacterial corrosion of mild steel;
      v. mesa corrosion; and
      vi. combinations thereof.

3. A system for identifying corrosion types, the system comprising:
   an examination subsystem that examines a solid surface having corrosion to obtain at least one image;
   a modeling subsystem that represents the image as a three-dimensional mathematical surface; and
   an analysis subsystem configured to:
      fit the three-dimensional mathematical surface to a parametric surface composed of one or more curved and/or polygonal shapes, where the parametric surface is selected from the group consisting of:
      a. parametric surface of n cones;
      b. parametric surface of n cut spheroids;
      c. parametric surface of n ellipsoids;
      d. parametric surface of n cylinders;
      e. parametric surfaces of n pyramids; and
      f. combinations thereof,
      where n represents the number of indicated shapes in the parametric surface;
      determine representative parameters from the parametric surface; and
      identify a corrosion type by the best fit of the representative parameters known to be correlated to a particular corrosion type; where in the analysis subsystem the corrosion type is selected from the group consisting of:
      i. $CO_2$ corrosion of mild steel;
      ii. $H_2S$ corrosion of mild steel;
      iii. oxygen corrosion of mild steel;
      iv. acid-producing bacterial corrosion of mild steel;
      v. mesa corrosion; and
      vi. combinations thereof.

4. A system for identifying corrosion types, the system comprising:
   an examination subsystem that examines a solid surface having corrosion to obtain at least one image by a device selected from the group consisting of optical microscopy, interferometry, Hall effect sensors, magnetic flux sensors, ultrasonic measurements and combinations thereof;
   a modeling subsystem that represents the image as a three-dimensional mathematical surface; and
   an analysis subsystem configured to:
      fit the three-dimensional mathematical surface to a parametric surface composed of one or more curved and/or polygonal shapes, where the parametric surface is selected from the group consisting of:
      a. parametric surface of n cones;
      b. parametric surface of n cut spheroids;
      c. parametric surface of n ellipsoids;
      d. parametric surface of n cylinders;
      e. parametric surfaces of n pyramids; and
      f. combinations thereof,
      where n represents the number of indicated shapes in the parametric surface;
      determine representative parameters from the parametric surface; and identify a corrosion type by the best fit of the representative parameters known to be correlated to a particular corrosion type; where the corrosion type is selected from the group consisting of:
i. $CO_2$ corrosion of mild steel;
ii. $H_2S$ corrosion of mild steel;
iii. oxygen corrosion of mild steel;
iv. acid-producing bacterial corrosion of mild steel;
v. mesa corrosion; and combinations thereof.

* * * * *